United States Patent
Hammer

(10) Patent No.: US 12,064,558 B2
(45) Date of Patent: Aug. 20, 2024

(54) COMPOSITE TEXTILE CUSHION

(71) Applicant: Fisher & Paykel Healthcare Limited, Auckland (NZ)

(72) Inventor: Jeroen Hammer, Auckland (NZ)

(73) Assignee: Fisher & Paykel Healthcare Limited, Auckland (NZ)

(*) Notice: Subject to any disclaimer, the term of this patent is extended or adjusted under 35 U.S.C. 154(b) by 724 days.

(21) Appl. No.: 17/255,369

(22) PCT Filed: Jun. 26, 2019

(86) PCT No.: PCT/NZ2019/050076
§ 371 (c)(1),
(2) Date: Dec. 22, 2020

(87) PCT Pub. No.: WO2020/009589
PCT Pub. Date: Jan. 9, 2020

(65) Prior Publication Data
US 2021/0260324 A1    Aug. 26, 2021

Related U.S. Application Data

(60) Provisional application No. 62/694,382, filed on Jul. 5, 2018.

(51) Int. Cl.
*A61M 16/06* (2006.01)

(52) U.S. Cl.
CPC ..... *A61M 16/0622* (2014.02); *A61M 2207/00* (2013.01)

(58) Field of Classification Search
None
See application file for complete search history.

(56) References Cited

U.S. PATENT DOCUMENTS

| | | | | |
|---|---|---|---|---|
| 3,493,645 | A | * | 2/1970 | Schmuckal ........ B29D 99/0053 277/575 |
| 4,406,847 | A | * | 9/1983 | O'Neal ................... B29C 43/18 264/262 |
| 4,915,395 | A | * | 4/1990 | Barteck .................. F16J 15/027 277/637 |
| 9,308,343 | B2 | | 4/2016 | Groll et al. |

(Continued)

FOREIGN PATENT DOCUMENTS

| | | |
|---|---|---|
| DE | 202010005143 | 7/2010 |
| EP | 2219719 | 8/2010 |

(Continued)

OTHER PUBLICATIONS

Patent Cooperation Treaty, International Search Report and Written Opinion, Application No. PCT/NZ2019/050076, dated Oct. 2, 2019, in 17 pages.

(Continued)

*Primary Examiner* — Emmanuel S Luk
(74) *Attorney, Agent, or Firm* — Knobbe, Martens, Olson & Bear, LLP

(57) ABSTRACT

A cushion for a respiratory therapy mask for contacting the face of a user. The cushion has a textile layer and a resilient material bonded to a surface of the textile layer. The resilient material is self-supporting to define a profile of the cushion, and the cushion has an opening for communication with a breathing chamber and delivery of fluid to the user.

19 Claims, 13 Drawing Sheets

(56) References Cited

U.S. PATENT DOCUMENTS

| | | |
|---|---|---|
| 9,782,553 B2 | 10/2017 | Brambilla et al. |
| 11,110,241 B2* | 9/2021 | Lockhart ............ A61M 16/0622 |
| 2002/0020416 A1* | 2/2002 | Namey ............... B29C 45/1676 |
| | | 128/205.25 |
| 2007/0175479 A1 | 8/2007 | Groll |
| 2009/0032018 A1 | 2/2009 | Eaton et al. |
| 2009/0032024 A1* | 2/2009 | Burz ................. A61M 16/0816 |
| | | 264/249 |
| 2011/0074120 A1* | 3/2011 | Namey, Jr. ............ B29C 45/561 |
| | | 277/650 |
| 2011/0162654 A1* | 7/2011 | Carroll ................. A61M 16/06 |
| | | 128/206.21 |
| 2014/0090649 A1 | 4/2014 | Groll et al. |
| 2014/0251338 A1 | 9/2014 | Asvadi et al. |
| 2016/0106943 A1* | 4/2016 | Gunaratnam ...... A61M 16/0611 |
| | | 128/205.25 |
| 2017/0049983 A1* | 2/2017 | Ellis ...................... B29C 70/345 |
| 2017/0361048 A1* | 12/2017 | Moiler ............. A61M 16/0825 |
| 2020/0114107 A1* | 4/2020 | Guney ............. A61M 16/0683 |

FOREIGN PATENT DOCUMENTS

| | | |
|---|---|---|
| EP | 2611489 | 7/2013 |
| EP | 2957314 | 12/2015 |
| EP | 3146991 | 3/2017 |
| EP | 3338846 | 6/2018 |
| WO | WO 2016/082001 | 6/2012 |
| WO | WO 2013/006913 | 1/2013 |
| WO | WO 2015/147947 | 10/2015 |
| WO | WO 2015/193408 | 12/2015 |
| WO | WO 2017/158471 | 9/2017 |
| WO | WO 2018/160077 | 9/2018 |

OTHER PUBLICATIONS https://www.padacheek.com/all-products (pdf of website accessed Dec. 7, 2020).

https://circadiance.com/products/ (pdf of website accessed Dec. 7, 2020).

https://www.remzzzs.com/hero (pdf of website accessed Dec. 7, 2020).

* cited by examiner

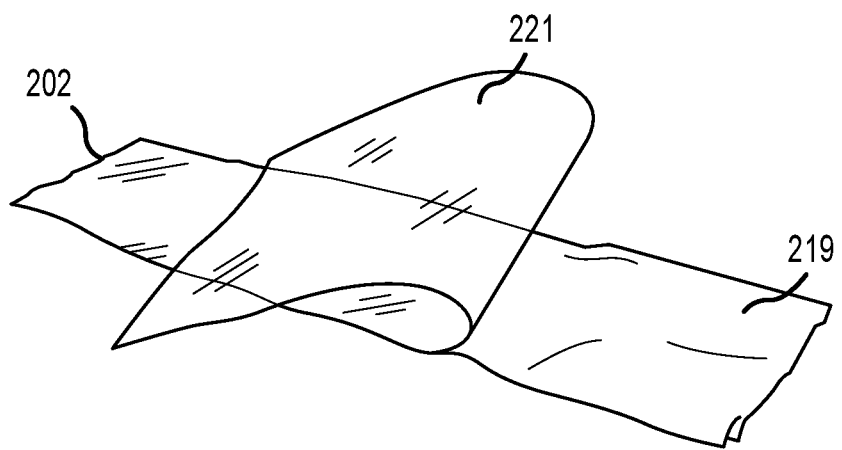
FIG.8
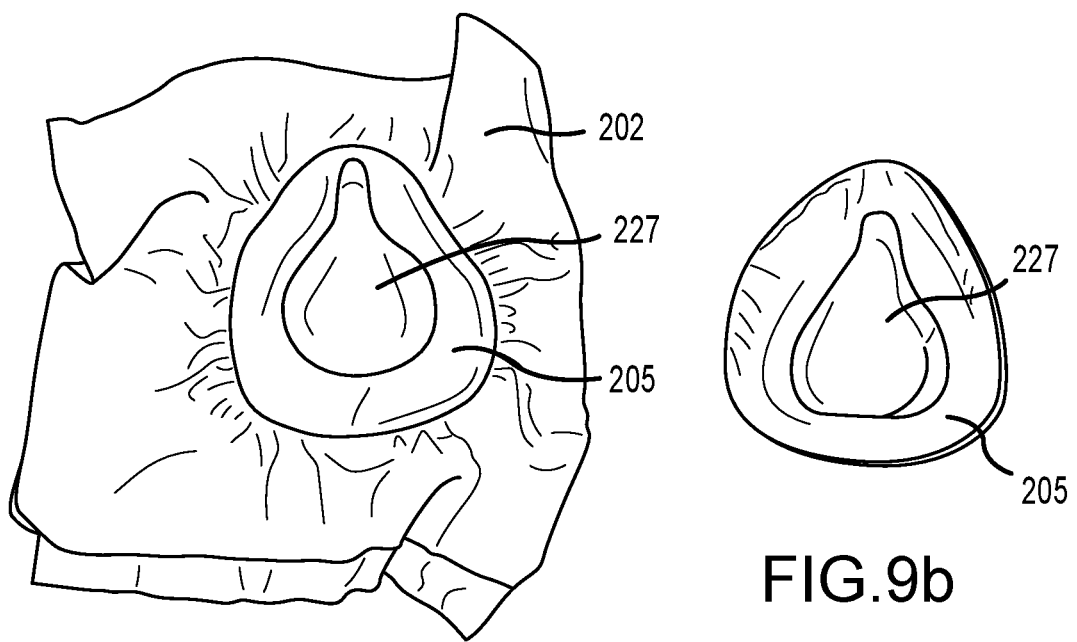
FIG.9a
FIG.9b

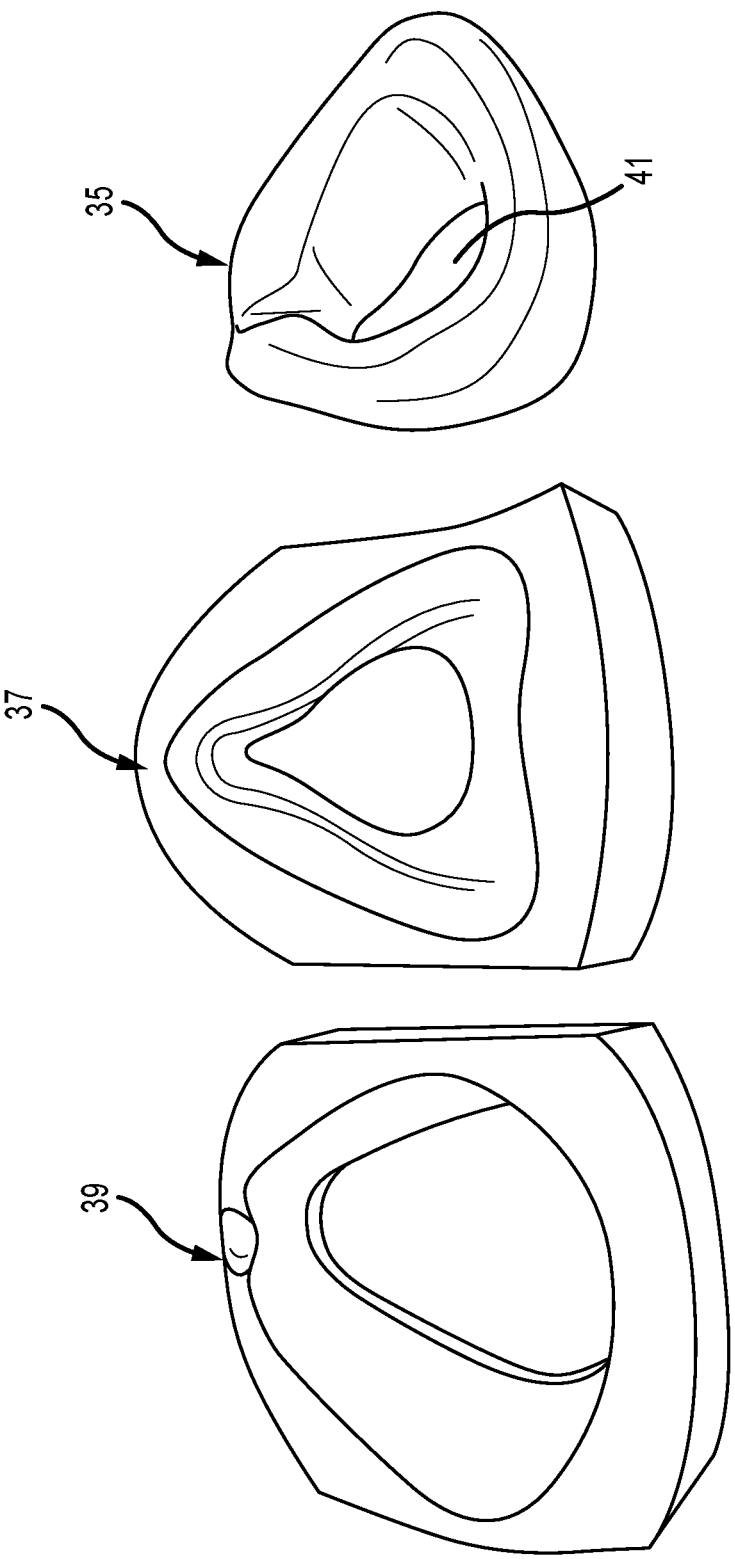

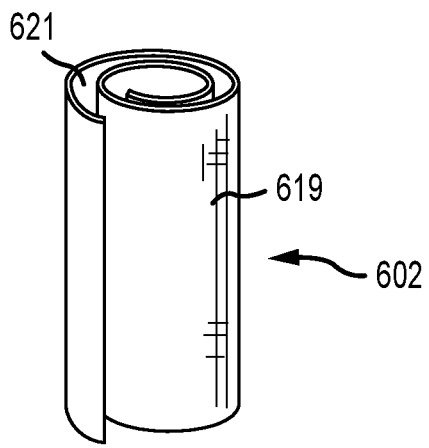
FIG.13
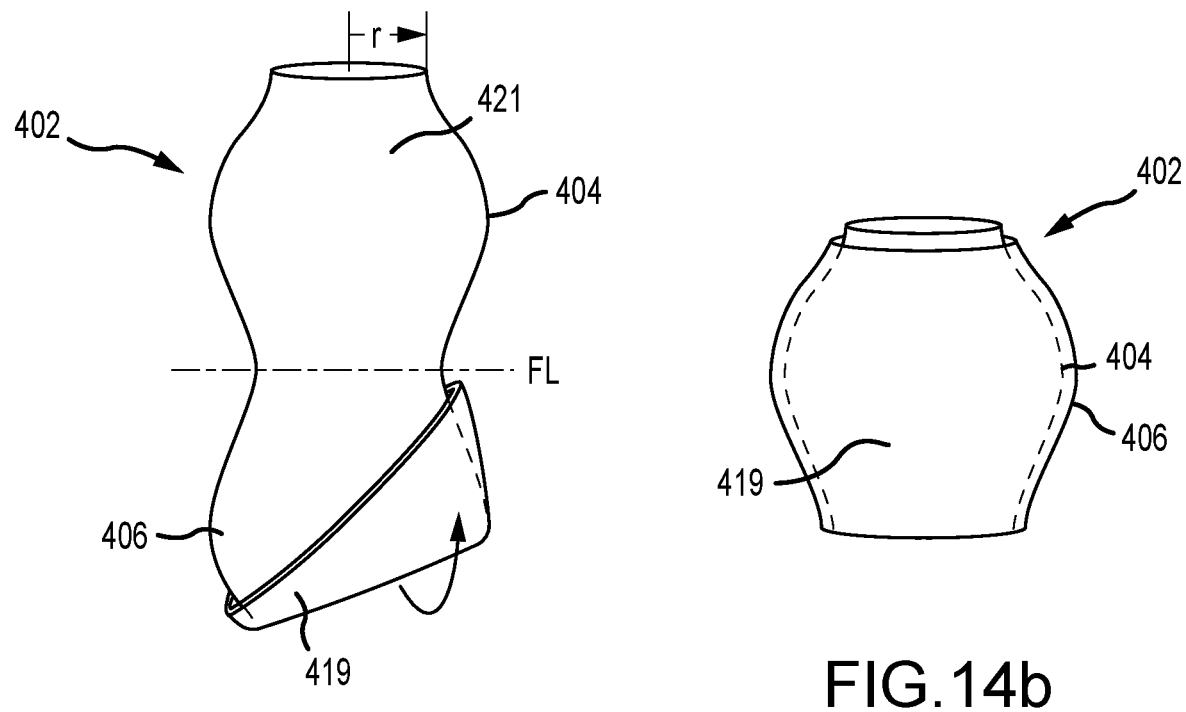
FIG.14a
FIG.14b

COMPOSITE TEXTILE CUSHION

BACKGROUND

Field of the Invention

The present disclosure generally relates to a respiratory patient interface, in particular to a textile and elastomeric composite cushion for such an interface and a method of producing a textile and elastomeric composite cushion.

Description of the Related Art

Respiratory masks are used to provide respiratory therapy to the airways of a person suffering from any of a number of respiratory illnesses or conditions. Such therapies may include but are not limited to continuous positive airway pressure (CPAP) therapy and non-invasive ventilation (NIV) therapy.

CPAP therapy can be used to treat obstructive sleep apnoea (OSA), a condition in which a patient's airway intermittently collapses during sleep, preventing the patient from breathing for a period of time. The cessation of breathing, or apnoea, results in the patient awakening. Repetitive and frequent apnoeas may result in the patient rarely achieving a full and restorative night's sleep.

CPAP therapy involves the delivery of a supply of continuous positive air pressure to the airway of the patient via a respiratory mask. The continuous positive pressure acts to keep the airway in an open position so the patient's breathing and sleep are not interrupted.

CPAP therapy requires the user to wear a respiratory interface which seals against a user's face, around their nose and/or mouth via a seal/cushion to deliver respiratory gas or gases such as air to a user a user under positive pressure. Respiratory masks are available in a range of styles including full-face, nasal, direct nasal and oral masks. The seal/cushion is held in place on the user's face by headgear which provides support to the respiratory interface such that it is held in a stable position relative to the user's face during use. Such respiratory masks may also be used to deliver NIV and other therapies.

Patients may be deterred from using CPAP therapy if they find the respiratory interface uncomfortable or if they find the appearance of the interface unattractive or intimidating because of its technical, medical appearance. Commonly respiratory interfaces are constructed from clear plastics and/or silicone, which give the interface a sterile appearance of a medical device. This undesirable appearance can reduce a user's initial engagement and make therapy acceptance more difficult.

Extended use of existing masks can also result in pressure sores caused by repetitive rubbing of the mask seal on the user's face. Some soft fabric-based masks are available and intended to provide improved comfort, however they lack structure making fitting of the mask less intuitive and more difficult, so the masks are susceptible to being poorly or incorrectly fitted.

It is an object of at least preferred embodiments of the present invention to address at least one of the abovementioned disadvantages and/or to at least provide the public with a useful alternative.

In this specification where reference has been made to other external documents, or other patent specifications, this is generally to provide a context for discussing features of the invention. Unless specifically stated otherwise, reference to such external documents or sources of information is not to be construed as an admission that such documents or such sources of information, in any jurisdiction, are prior art or form part of the common general knowledge in the art.

SUMMARY OF THE INVENTION

In a first aspect, the present disclosure relates to a cushion for a respiratory therapy mask for contacting the face of a user. The cushion has an opening for communication with a breathing chamber and delivery of fluid to the user. The cushion comprises a textile layer and a resilient material bonded to the textile layer. The textile layer and resilient material together define a profile of the cushion, the resilient material biasing the textile layer towards the cushion profile.

In an embodiment, the cushion is self-supporting.

In an embodiment, the resilient material comprises an elastomer, for example, the elastomer may comprise silicone.

In an embodiment, the resilient material is substantially impermeable to air.

In an embodiment, the textile layer forms an outer surface of the cushion for contacting the face of a user.

In an embodiment, the resilient material comprises an elastomeric layer bonded to a surface of the textile layer. In an embodiment, resilient material comprises an elastomer and the textile layer is impregnated with the elastomer. In an embodiment, the resilient material forms an inner layer of the cushion.

In an embodiment, the textile layer is formed from a textile tube. A second textile layer may be bonded to the resilient material, the second textile layer forming an inner surface of the cushion. The second textile layer may be formed from a textile tube. In an embodiment, the second textile layer is formed from the same textile tube as the first textile layer.

In an embodiment, the second textile layer and the first textile layer are formed from a continuous textile tube.

The textile tube(s) may comprise a cylindrical tube in which a radius of the textile tube(s) may be constant or may vary along a length of the tube. Alternatively, the textile tube(s) may have a cross sectional shape that varies along a length of the tube. For example, the cross sectional shape may transition from circular to triangular along the length of the textile tube.

In an embodiment, the cross sectional area of the tube varies along the length of the textile tube. For example, the cross sectional area may vary from a first cross sectional area to a second cross sectional area along the length of the textile tube, the first cross sectional area being larger than the second cross sectional area. In a further embodiment, the textile tube(s) comprise a tube transitions from a circle of a first radius to a circle of a second radius along the length of the textile tube. The first radius may be larger than the second radius.

In an embodiment, edges of the cushion comprise cut edges.

In an embodiment, the textile layer(s) may comprise one or more of: an air permeable textile, an absorbent textile, a knitted textile, a three dimensional knitted textile tube, and a woven textile. In an embodiment, the density of threads or fibres of the textile varies in different portions of the cushions, for example, the density of threads or fibres of the textile may be lower at wider portions of the cushion where the textile is held in a stretched state by the resilient material. The textile is preferably free from embedded elastic threads, thereby reducing the recovery of the textile.

In an embodiment, the textile has an elastic recovery of 0-20%, more preferably less than 10%.

In an embodiment, the textile layer(s) comprise one or more of: polyester, nylon, cotton, wool, rayon, silk, viscose, hemp, polyester. The textile layer(s) may be patterned or have a plurality of decorative cut-outs. In an embodiment, the cushion comprises one or more air permeable cushion portions free of the resilient material.

In a second aspect, the present disclosure relates to a cushion for a respiratory therapy mask for contacting the face of a user. The cushion has a profile with an opening for communication with a breathing chamber and delivery of fluid to the user. The cushion is self-supporting and comprises a textile layer and a resilient material bonded to the textile layer. The resilient material biases the textile layer towards the cushion profile.

In an embodiment, the resilient material comprises a layer bonded to a surface of the textile layer. The cushion may have any one or more of the properties or features described above in relation to the first aspect In a third aspect, the present disclosure relates to a cushion module comprising the cushion as described above in relation to the first or second aspects, and a housing forming at least a portion of a breathing chamber, the cushion being attached to the housing.

In an embodiment, the housing includes a connector for connecting the housing to a frame.

In a fourth aspect, the present disclosure relates to a respiratory mask, comprising: a frame configured to connect to headgear, and the cushion module described above in relation to the third or fourth aspects, the cushion module being arranged to connect to the frame.

In a fifth aspect, the present disclosure relates to a cushion pre-form for forming into a cushion for a respiratory therapy mask, the pre-form comprising a textile layer and a curable substance applied to a surface of the textile.

In an embodiment, the pre-form is a tube. The tube may have a radius that varies along a length of the tube. In an embodiment, a cross sectional shape of cross sectional area of the tube varies along a length of the tube.

In an embodiment, the pre-form tube is a double walled tube with an inner textile layer and an outer textile layer, with the curable substance between the two layers. The inner and outer textile layers may be formed from a continuous tube folded over on itself.

In an embodiment, the curable substance comprises silicone.

In an embodiment, the textile comprises a knit.

In an embodiment, the cushion pre-form is suitable for forming into the cushion described above in relation to the first and second aspects.

In a sixth aspect, the present disclosure relates to method of manufacturing a cushion for a respiratory therapy mask for contacting the face of a user, comprising the steps of:
  applying a curable substance to a textile to form a cushion pre-form;
  shaping the cushion pre-form into a cushion profile, and curing the curable substance to bias the cushion towards the cushion profile.

In an embodiment, the textile is a textile tube. In an embodiment, the curable substance is applied to an outer surface of the textile tube.

In an embodiment, shaping the preform includes folding a first end of the textile tube outwards and over the remainder of the length of the textile tube towards a second end of the textile tube, creating a folded double walled textile tube, with the curable substance disposed between the two textile wall layers.

In an embodiment, the method further includes the step of placing the pre-form in a mold tool.

In an embodiment, the method further includes the step of removing excess material from the pre-form or cured cushion to facilitate connection of the cushion to a housing of a cushion module.

In an embodiment, the step of shaping the pre-form includes stretching the preform over a mold. In an embodiment the pre-form has a shape that corresponds to the shape of a mold over which the pre-form is placed.

This invention may also be said broadly to consist in the parts, elements and features referred to or indicated in the specification of the application, individually or collectively, and any or all combinations of any two or more said parts, elements or features. Where specific integers are mentioned herein which have known equivalents in the art to which this invention relates, such known equivalents are deemed to be incorporated herein as if individually described.

The term 'comprising' as used in this specification and claims means 'consisting at least in part of'. When interpreting statements in this specification and claims that include the term 'comprising', other features besides those prefaced by this term can also be present. Related terms such as 'comprise' and 'comprised' are to be interpreted in a similar manner.

It is intended that reference to a range of numbers disclosed herein (for example, 1 to 10) also incorporates reference to all rational numbers within that range and any range of rational numbers within that range (for example, 1 to 6, 1.5 to 5.5 and 3.1 to 10). Therefore, all sub-ranges of all ranges expressly disclosed herein are hereby expressly disclosed.

As used herein the term '(s)' following a noun means the plural and/or singular form of that noun. As used herein the term 'and/or' means 'and' or 'or', or where the context allows, both.

BRIEF DESCRIPTION OF THE DRAWINGS

Embodiments will now be described by way of example only and with reference to the accompanying drawings in which:

FIG. 8 illustrates arrangement of a resilient sheet over a textile sheet to create a pre-form;

FIGS. 9(a) and 9(b) show the formation of a cushion from the pre-form of FIG. 8, where FIG. 9(a) shows the cured pre-form removed from the mold, and FIG. 9(b) shows the excess material trimmed from the periphery of the cushion;

FIGS. 10(a) to 10(c) show mould parts for forming the composite cushion of FIGS. 2 to 5, where FIGS. 10(a) and 10(b) are outer mold parts, and FIG. 10(c) is an inner mold part;

FIG. 11(a) shows a composite tube with an inner textile layer and an outer curable layer, FIG. 11(b) illustrates the step of folding the tube over itself, and FIG. 11(c) shows the resulting tubular preform with inner and outer textile layers and an intermediate curable layer;

FIG. 10(a) shows the unshaped pre-form in the opening of the mold part, FIG. 10(b) shows the pre-form being folded over itself, and FIG. 10(c) shows the preform snug around the inner mold part for curing;

FIG. 13 illustrates an alternative method of forming a pre-form tube by rolling a composite sheet over itself;

FIGS. 14(a) and 14(b) illustrate the process of creating a contoured pre-form with inner and outer textile layers, where FIG. 11(a) shows a composite tube with a varying diameter with an inner textile layer and an outer curable layer, and FIG. 14(b) shows a tubular preform with a varying radius with inner and outer textile layers and an intermediate curable layer;

FIG. 15(a) shows two flat sheets stitched together, FIG. 15(b) shows the pre-form being folded over itself, and FIG. 15(c) shows a tubular preform with inner and outer textile layers and an intermediate resilient layer;

FIG. 16(a) shows the unshaped pre-form in the opening of the mold part, FIG. 16(b) shows the pre-form being folded over itself, FIG. 16(c) shows the preform snug around the mold part for curing, and FIG. 16(d) shows the cured cushion on the mold inner with excess material removed;

FIG. 16(a) shows the unshaped pre-form in the opening of the mold part, FIG. 16(b) shows the pre-form being folded over itself, and FIG. 16(c) shows the pre-form snug around the mold part for curing; FIG. 18(a) shows the mold inner and fitted pre-form being placed between two mold outer parts, FIG. 18(b) shows the cured cushion removed from the outer mold parts with excess material trimmed, and FIG. 18(c) shows the removed cushion partly deformed in a manner that illustrates its resilience.

DETAILED DESCRIPTION

Various embodiments and methods of manufacture will now be described with reference to FIGS. 1 to 18(c). In these figures, like reference numbers are used to indicate like features. Where several embodiments are illustrated, like reference numbers may be used for like or similar features in subsequent embodiments but with the addition of a multiple of 100, for example 2, 102, 202, etc.

Directional terminology used in the following description is for ease of description and reference only, it is not intended to be limiting. For example, the terms 'front', 'rear', 'upper', 'lower', and other related terms refer to the location of a part or portion of a respiratory mask relative to a user, where 'front' refers to a location that is distal to the user (when the mask is in use) and 'rear' refers to a location that is proximal to the user by comparison. The terms 'upper' and 'lower' refer to the location of a part or component of a mask relative to the rest of the mask when the mask is in use and the user is sitting in an upright position.

Figure 1:
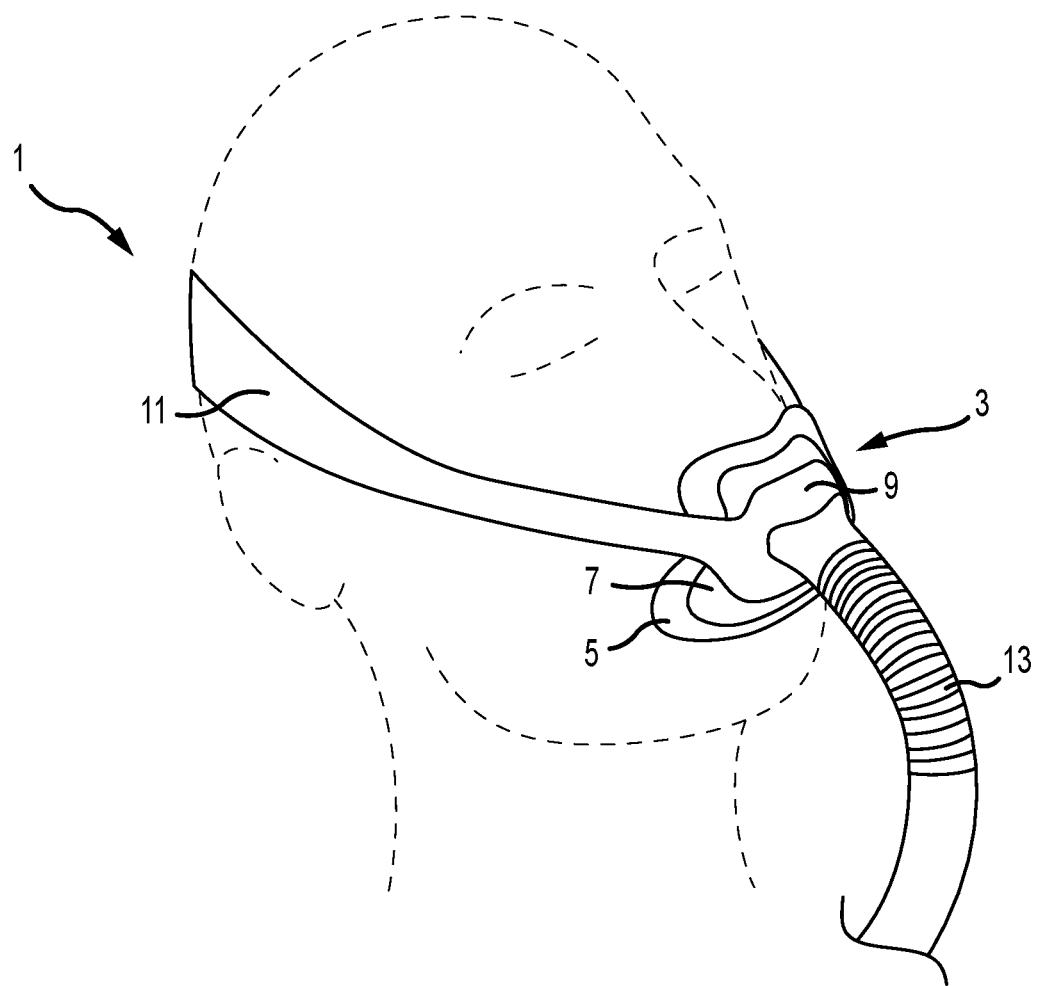
FIG. 1 is a schematic showing a respiratory user interface including a head strap and cushion module, connected to a supply conduit.

FIG. 1 schematically shows an interface assembly 1 for a respiratory system. The interface assembly 1 comprises a mask having a cushion module 3 with a cushion 5 attached to a housing 7, and a frame or frame assembly 9. The interface 1 also includes headgear 11 for securing the mask on the user. In some configurations such as the one shown, the housing 7 is coupled to the frame 9 and the headgear is in turn coupled to the frame 9. However, other arrangements are possible such as the headgear directly attaching to the housing 7.

Figure 2:
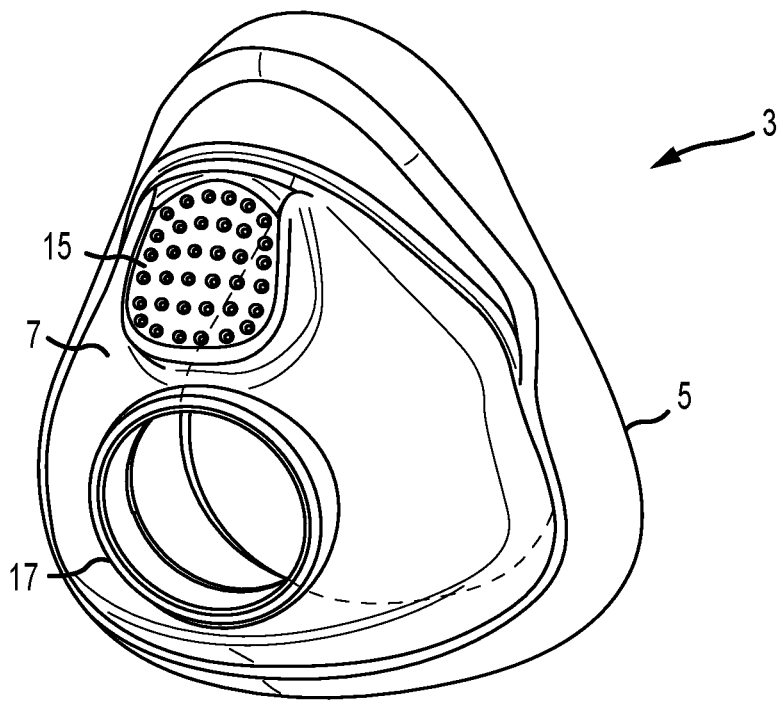
FIG. 2 is a perspective view of a cushion module having a composite cushion.
Figure 3:
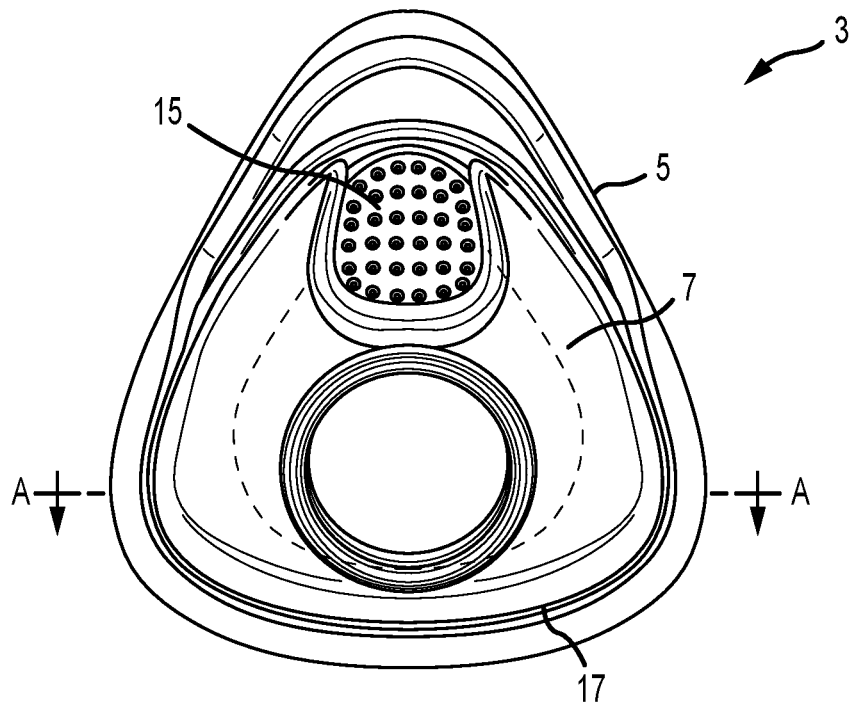
FIG. 3 is a front view of the cushion module of FIG. 2.

Referring to FIGS. 1 to 3, the cushion module 3 is configured to contact the face of a user, sealing around the user's mouth and over the lower part of the nose. A breathing chamber is defined by one or more of the housing 7, cushion 5, and frame 9. The cushion module 3 is operatively connected to a flexible supply conduit such as a tube 13, which connects to a CPAP system or other respiratory system to provide gas flow to the breathing chamber. In the embodiment shown, the conduit 13 extends from a central connector at the front of the housing 7. The conduit 13 may be connected to the housing 7 either directly or via a suitable connector, such as a hollow elbow, and may swivel about one or more swivel axes relative to the cushion module 3 to allow the path of the conduit 13 to adapt to the sleeping position of the user.

Exemplary full face cushion modules 3 and corresponding cushions 5 are shown in the drawings and described herein. However, these examples are not intended to be limiting. Features of the exemplary cushion and cushion module embodiments described herein can be applied to other types of mask or cushion module configurations including nasal masks or direct nasal masks. The cushion 5 may be removably attached to the housing 7, permanently attached to the housing 7, or may be integrally formed with the housing 7.

As best illustrated in FIGS. 2 to 6, the composite cushions 5, 105 described herein consist of a flexible wall comprising a perimeter portion 23, 123 that extends from the housing 7, 107, and a user contacting portion 25, 125 curving inwards from the perimeter portion, although cushions of other shapes are envisaged. The cushion 5, 105 has an opening 27, 127 defined by the flexible wall, for fluid communication with the breathing chamber of the housing 7 107 for delivery of air to the user.

The flexible wall of the cushion 5 is preferably shaped to extend over the lower part of a user's nose, and around and under their mouth, with the user contacting portion 25, which has a three dimensional contour that approximates the user's facial contours. In at least one configuration, the flexible wall of the cushion can be alternatively shaped to extend under the user's nose, sealing with an underside or base of the user's nose, and around and under their mouth. In at least one configuration, the flexible wall of the cushion can be alternatively shaped to extend over a part of the user's nose and under their mouth, sealing around the user's nasal passages, with the user contacting portion having a three dimensional contour that approximates the user's facial contours. Different shaped cushions will be better suited to different users. For example a child will generally require a smaller and/or shaped cushion to an adult.

The cushions 5, 105 are composite material cushions. That is, their flexible wall comprises more than one material, namely a textile layer 19 119 and a resilient material 21 121, which is bonded to a surface of the textile layer. The thickness of the resilient layer may be substantially constant or may vary in different parts of the cushion 5, for example being thicker in regions where more strength or less flexibility is required.

The resilient material 21, 121 has a thickness sufficient such that the cushion has a profile which is self-supporting but which provides compliance or cushioning by flexing of the wall 23, 25, for example when pressed into the face of a user.

Figure 4:
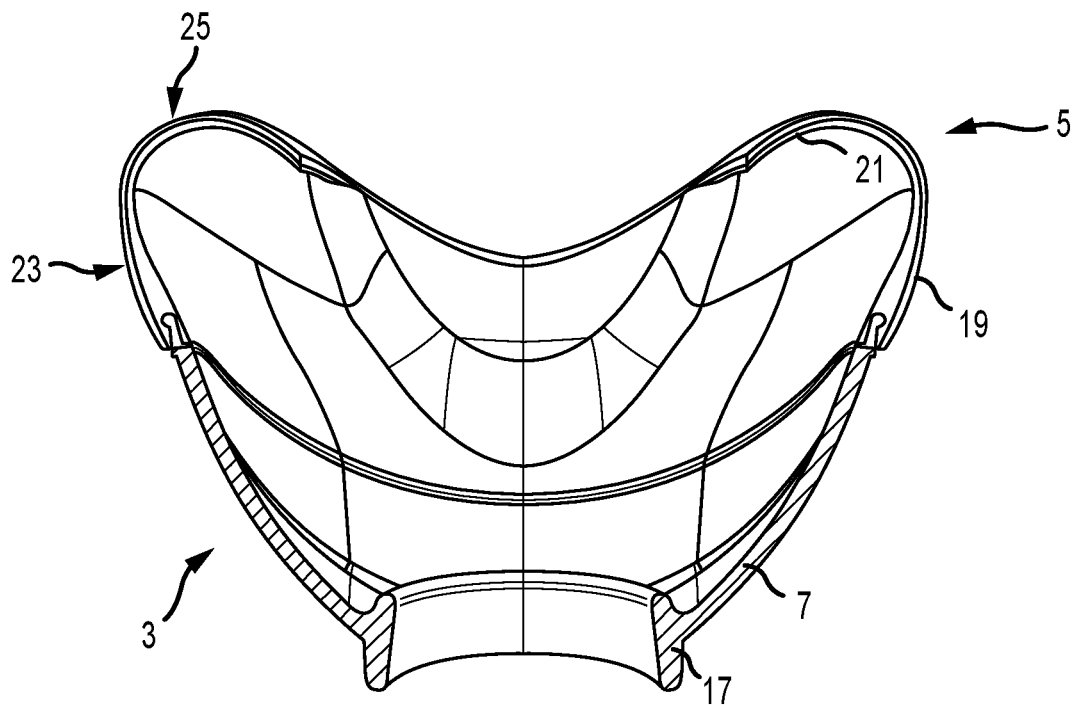
FIG. 4 is a top section view taken along plane AA of FIG. 3, showing a composite cushion with a single textile layer.

In the embodiment shown in FIG. 4, the cushion wall comprises a two layer laminate having a resilient inner layer 21 and a textile outer layer 19 for contacting the face of a user. The outer textile layer 19 in this arrangement creates an outer textile surface and gives a less clinical appearance to the cushion module, more suited to the aesthetics of a bedroom or home environment.

The outer textile surface may provide a soft-touch surface for improved comfort, along with improved breathability of the outer layer due to the porosity of the textile to air and water, improved temperature regulation, and improved absorption and/or moisture wicking. The outer textile surface may improve the health of a patient's skin, for example, by allowing improved skin thermal regulation, desquamation, hydration, and atmospheric absorption of oxygen.

Typically, a standard silicone seal is a poor absorber of moisture, whereas a textile outer layer can absorb or wick moisture away from the skin of the user. Moisture on the skin significantly increases the likeliness of skin damage caused by wearing a patient interface. In addition, absorption of moisture by the skin worsens friction as skin friction increases with more hydrated skin.

Figure 5:
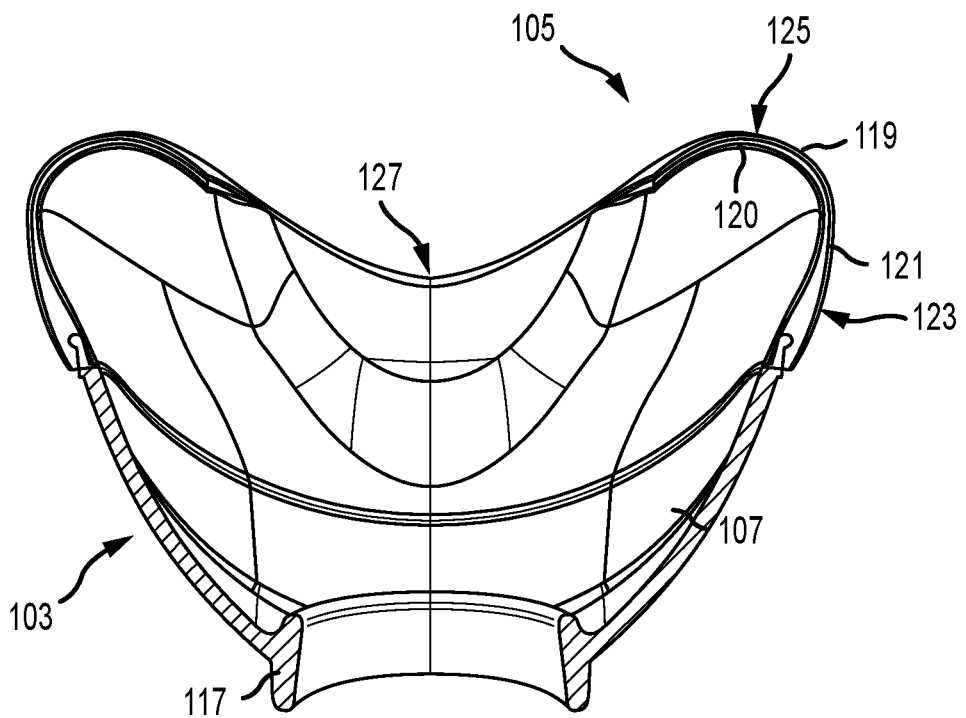
FIG. 5 is a section view corresponding to FIG. 4, but showing a composite cushion with two textile layers.
Figure 6:
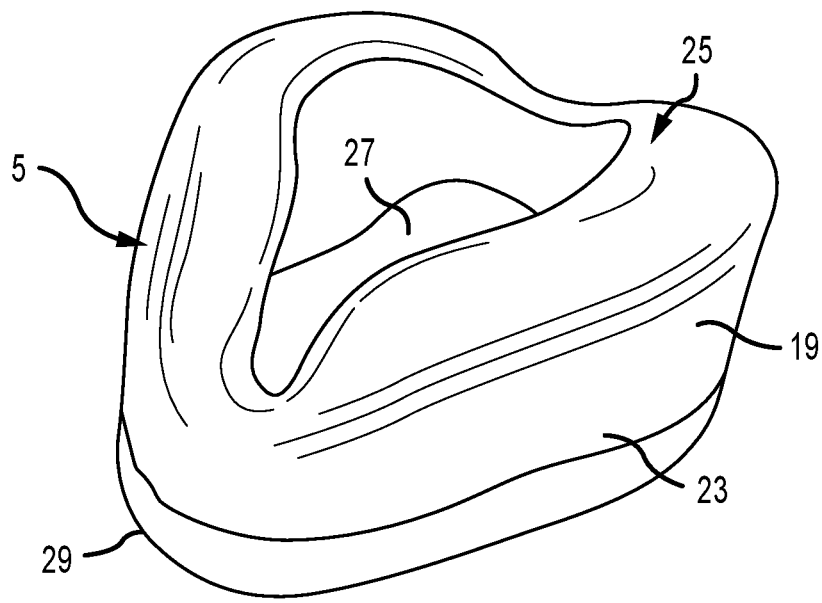
FIG. 6 is a perspective view of one form of composite cushion.

In an alternative embodiment shown in FIG. 5, the cushion wall is a three layer laminate having a first textile layer 119 providing an outer layer for contacting the face of a user, a second textile layer 120 providing an inner surface of the cushion, and an intermediate resilient layer 121 between the two textile layers 119, 120 and bonded to the two textile layers.

In other embodiments, the seal could have two layers in some areas, and three layers in others to provide different properties in different parts of the cushion. The inclusion of more than one textile layer or more than one resilient layer enables a higher degree of customisation of properties of the cushion 105, for example, in different regions of the cushion. Some embodiments may have increased thickness around the outer perimeter of the cushion to better support the outer wall of the seal. Increased thickness at or towards a perimeter of the cushion may facilitate connection of the cushion to the housing, for example by providing a stronger and/or more resilient coupling between the cushion and the housing. Increased thickness around the inner perimeter of the cushion, i.e. the portion of the cushion defining the opening through which a user breathes gas may also be desirable. If the wall of the cushion around said opening is too thin, for example, too thin to support its profile when the mask is pressurized, this can cause instability resulting in vibration of the cushion wall and/or the inner wall blowing outwards. This can be a particular problem for under-nose seals.

One method for providing additional layers of material at the outer perimeter or inner opening of the cushion is to fold the cushion wall 402 on itself adjacent the edge of the cushion—outwards at the perimeter of the cushion, or inwards at the inner opening.

Advantageously, embodiments with multiple textile layers may also require less resilient material. Resilient materials such as silicone can be expensive, so including additional textile layers can reduce the cost of the mask. The cushion resilient layer(s) 21, 121 preferably comprises an elastomer such as cured silicone but alternatively may comprise any other suitable laminate material or a prefabricated resilient layer. Possible alternative materials include polyurethane, latex, and rubber.

The resilient material 21, 121 may be bonded to the textile layer(s) 19, 119, 120 by being partly or fully impregnated in the textile layer, or may be adhered to the textile layer with an adhesive, or may be over-moulded onto the textile layer(s). The extent of impregnation of the textile with the silicone depends on the desired properties of the seal/cushion. The textile may be fully impregnated, with silicone distributed throughout the textile layer, create a silicone finish on both sides in instances where a non-textile surface finish is desired, such as having a silicone surface finish for ease of cleaning, and low risk of allergic reactions. Partially impregnating the textile will bond the resilient layer to the textile but the surface finish will be the one provided by the textile, as may be desired for comfort reasons. With only minimal impregnation of the textile, the resulting composite more distinct textile and silicone layers.

The combination of fabric and silicone in the composite cushion advantageously provide the cushion with benefits of both fabric and silicone. For example, the silicone provides durability and increases the UV stability of the cushion, whereas the textile provides tear resistance. The resilient material is preferably substantially impermeable to air such that the cushion creates a seal between the breathing chamber and the user when the cushion is in contact with the face of the user. Alternatively the resilient material 21, 121 may have some inherent air permeability or the resilient layer 21, 121 may have regions that are air permeable. Air permeable regions of the cushion 5, 105 may be produced by controlling the location of material forming the resilient layer 21, 121. For example, bias flow holes can be included in the cushion by selectively forming regions that do not include the resilient material. The resilient material can be prevented from occupying these regions or removed from these regions, allowing gas to escape from the pressurised inside of the cushion module and out the seal via the breathable textile layer 19, 119. In some configurations, these regions can be disposed on a peripheral region of the cushion so that the gas can escape or be directed away from the user's face.

The textile layer(s) 19, 119, 120 may comprise any suitable textile, for example a textile comprising one or more of cotton, wool, rayon, silk, viscose, hemp, and polyester or other synthetic fibres. The textile may include additives to enhance its properties. For example, silver particles can be included for anti-microbial benefits. Preferably the textile is air permeable, for example it may be knitted or woven, and may have one or more features such as being moisture absorbing, having a smooth, soft, or plush texture, and having a low propensity to wrinkling, depending on the desired characteristics of the cushion 5, 105. The textile may be inelastic or elastic.

Figure 7A:
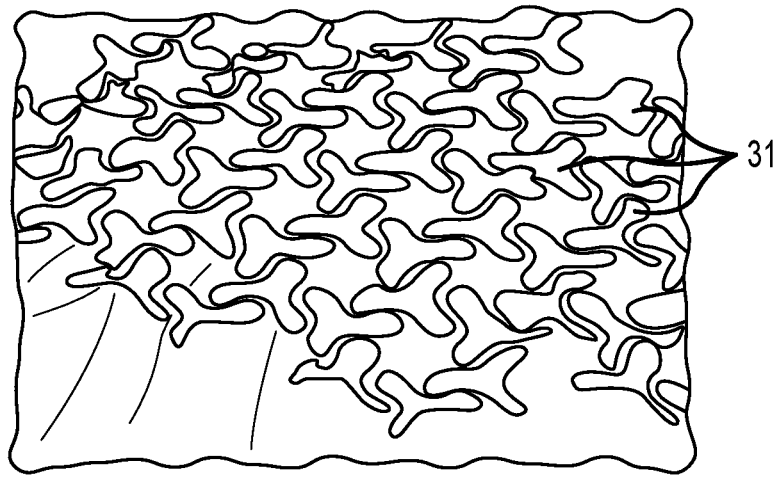
FIGS. 7(a) and 7(b) show exemplary textile cut-out patterns.
Figure 7B:
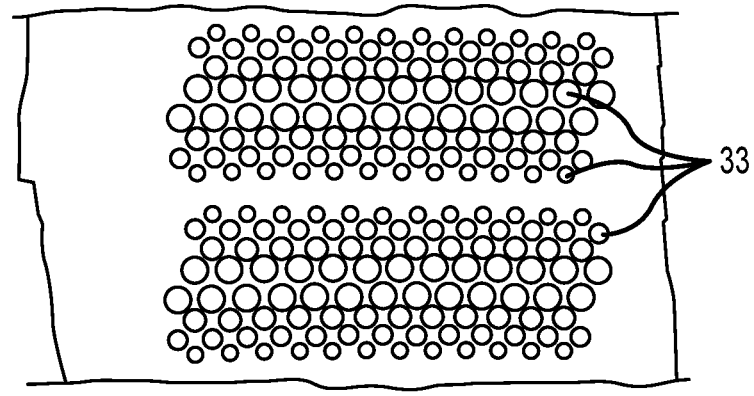

The textile may be of a block colour, may be patterned or printed, and/or may have decorative or functional cut-outs such as those shown in FIGS. 7(*a*) and 87(*b*). These cut-outs 31, 33 may be shaped and arranged to improve the health of a patient's skin, for example, by allowing improved skin thermal regulation, desquamation/exfoliation, hydration, and atmospheric absorption of oxygen. The cut-outs 31, 33 may be positioned to provide improved venting from the breathing chamber in targeted regions, may be included to reduce the weight of the cushion 5, 105 while still maintaining the aesthetic and comfort benefits of having a textile layer, and/or may be shaped and positioned to provide greater flexibility in the cushion 5, 105 in the region of the cut-outs. Alternatively or additionally the cut-outs may be for aesthetic reasons, potentially reducing stigma associated with the respiratory mask. FIG. 7(*a*) shows one possible cut-out pattern consisting of a series of rotated and translated Y-shaped cut-outs 31 across the surface of the textile. FIG. 7(*b*) shows an alternative embodiment with an array of circular cut-outs 33 with the size of the cut-outs varying in different places over the surface of the textile. Where cut-outs 31, 33 are provided in the textile layer for venting purposes, all or some of the cut-outs may be located at a region of the cushion where there is no resilient material or where there are openings in the resilient layer 21, 121 to allow the passage of gas through the resilient layer 21, 121 and the textile cut-outs. Alternatively, there may be cut-outs or other vents or openings that extend through one or both textile layers and through the resilient layer. That is, the cushion 5, 105 may have one or more air impermeable regions.

The textile layer(s) 19, 119, 120 may be coated with a thin outer coating if desired. For example, a thin outer coating of silicone for waterproofing, or a metallic coating for reflective properties. This coating may include additives such as anti-microbial additives, to enhance its properties. For example, silver particles can be included for anti-microbial benefits.

With reference to FIG. 8, the cushions 5, 105 described herein may be advantageously manufactured from a pre-form. FIG. 8 shows an exemplary pre-form 202 in which a curable elastomeric layer 221 is adhered (but not cured) to a textile layer 219. A thin plastic sheet may be used to apply the silicone to the textile layer 219, with the silicone layer 221 attached to the side of the plastic sheet facing the textile layer 219. Once the silicone is adhered to the textile layer 219, the plastic sheet is removed by peeling the sheet back. Alternatively, the curable elastomeric layer 221 can be sprayed onto the textile layer 219. This can for example be done using an airbrush. Alternatively, the curable elastomeric layer 221 can be physically applied to the textile layer 219. This can be by means of a brush, sponge and/or knife. The resulting pre-form sheet 202 is suitable for manufacturing a two-layer cushion 5 such as the one shown in FIG. 4. The pre-form 202 may optionally further comprise a top textile layer for manufacturing a three-layer composite cushion 105 such as the one shown in FIG. 5.

To form the pre-form sheet 202 into a cushion, the pre-form sheet 202 is formed into a three dimensional shape by pressing it into a mould tool. A suitable three-piece mold tool is shown in FIGS. 10(*a*) to (*c*). The mold tool parts 35, 37, 39 are shaped according to the desired cushion shape. The pre-form 202 is stretched over an inner mold part 35, which is then pressed between two outer mold parts 37, 39. The mold tool environment is heated and/or pressurised to cure the resilient layer 221, permanently bonding the resilient layer 221 to the textile layer 219.

As illustrated in FIGS. 9(*a*) and 9(*b*), the formed cushion 205 is then removed from the mold tool 25, 27, 29 and excess material trimmed from the cushion, for example by cutting the material with a blade or laser cutting. The use of a pre-form as an intermediate product between the raw materials and the formed cushion advantageously enables the pre-forms to be made and stored until required or for the pre-forms to be at one site and transported to another site for forming into the cushion. However, it is to be appreciated that in other embodiments, the cushion could be formed in a continuous process from raw materials in which the pre-form is used to form the cushion immediately or shortly after it is made.

Depending on the nature and thickness of the resilient layer(s) 221 and textile layer(s) 219, and the size and shape of the cushion 205, pressing a flat sheet in a three dimensional mold can result in the textile wrinkling or stretching unevenly during curing.

Figure 11C:
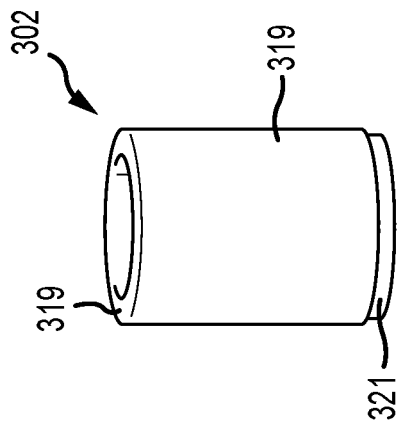
FIGS. 11(a) to 11(c) illustrate steps of folding a layered tube over itself to create a cylindrical pre-form with inner and outer textile layers, where
Figure 11B:
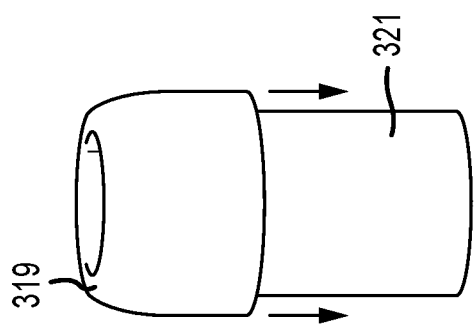
Figure 11A:
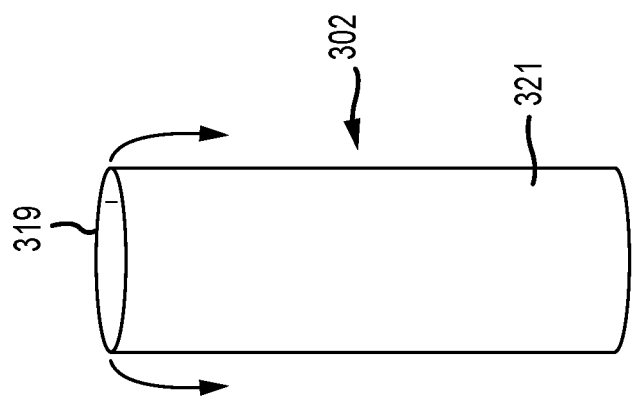

An alternative pre-form 302 is illustrated in FIGS. 11(*a*) to (*c*). In this pre-form, the textile layer 319 is in the form of a tube. The tube is a cylindrical tube. An outer surface of the textile tube 319 is coated with a curing agent 321 such as a silicone laminate, suitable for forming a resilient layer. The textile tube 319 may be created from a textile sheet, for example by adhering or stitching edges together to form a tube, or it may be formed as a tube using a process such as three-dimensional knitting or circular braiding.

FIG. 11(*a*) illustrates a textile tube pre-form 302 with a curable outer coating 321. This coated tube may be suitable for manufacturing a two-layer cushion 5 such as the one shown in FIG. 4. Alternatively, the pre-form tube 302 may be rolled over on itself as shown in FIGS. 11(*b*) and 11(*c*) to create a second concentric textile tube. The textile 319 is now on both the inner and outer surfaces of the tube, with the curable coating 321 between the two textile layers 319. In this form, the pre-form 302 is suitable for manufacturing a three-layer cushion 105 such as the one shown in FIG. 5.

Rather than the method of folding a single tube over onto itself to create a cylindrical pre-form with inner and outer textile layers, two concentric textile tubes could be used, with the outside of a first, inner tube and/or the inside of a second, outer tube being coated in the curing agent. The second tube is placed around the first tube so that the outer curing agent layer of the first tube, and/or the inner curing agent layer of the second tube form a central curing layer. Alternatively, the pre-form could be manufactured using knitting machines to create two concentric textile tubes, with nozzles between the tubes to spray the curing material. This would result in a continuous manufacturing process for the tube. The inner and outer textile tubes may have the same diameter or the second tube may fabricated with a slightly larger diameter than the first tube so it can be more easily slipped over the outside of the first tube.

FIG. 13 illustrates an alternate way of forming a cylindrical pre-form. A single sheet of textile 619 can be partially coated on one side with curing agent 621. The coated textile sheet can then be rolled around itself to form a tubular preform 602 with a central curing agent layer and inner and outer textile layers 619.

Figure 12A:
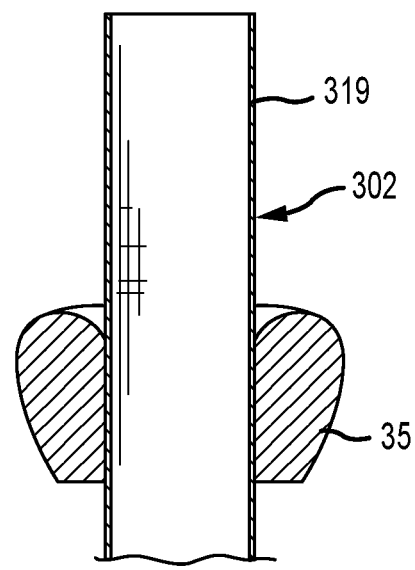
FIGS. 12(a) to 12(c) illustrate a method of placing a cylindrical pre-form over the inner mold part of FIG. 10(c), where
Figure 12B:
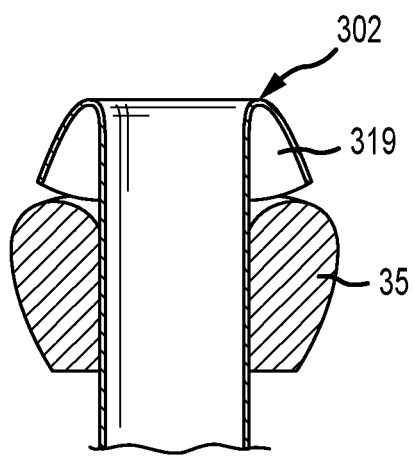
Figure 12C:
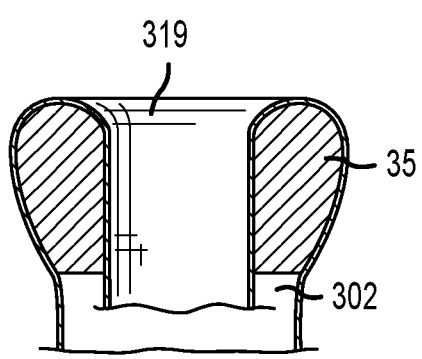

FIGS. 12(*a*) to 12(*c*) illustrate a method for forming the tubular pre-form 302 of FIG. 11(*c*) (or the pre-form 602 of FIG. 13) into a cushion. The composite pre-form 302 is placed through the opening 41 of the inner mold part 35, then folded from the top, down over itself and over the mold part 35, as shown in FIGS. 12(*a*) and 12(*b*) with the textile stretching in places as necessary to accommodate the inner mold part 35. The outer mold parts 37, 39 are then placed around the inner mold 35 and pre-form and heated to cure the curing agent and bond the resilient material to the textile layers. The cured resilient material holds the shape of the mold when removed and preferably holds the stretched regions of the textile in their stretched state.

Various types of textiles may be suitable for use in the mold, for example braded, woven, or knitted textiles. The manner in which the tube (or other pre-form) stretches over the mold part 35 will depend on the nature of the textile. In a knitted textile, the textile will deform or 'stretch' under load, with threads or fibres moving apart at wider regions of the mold tool such that the density of the threads of fibres is lower in those stretched regions and higher in the unstretched or lesser stretched regions. The textile is then held in this deformed state by the resilient material once it is cured.

Knitted textiles are particularly suited to applications where a high degree of stretch is required in some regions. This is because knitted textiles exhibit good stretch properties due to the interlocking looped fibres formed during knitting, which can straighten under load. In contrast, braided and woven textiles, depending on the fibre type and density, have lower stretch due to the straight weave of the fibres. Further, most textiles have different stretch properties in warp and weft direction, and the textile is preferably laid up relative to the mold depending on the desired stretch characteristics.

The stretch of a textile differs from the recovery properties of a textile. Recovery is a measure of how easily the textile recovers to its original shape after stretching. Preferably the textile layers in the cushions described herein, particularly those formed from planar or cylindrical pre-forms, have a low level of recovery. For example, the textile forming the textile layer(s) preferably has an elastic recovery of less than 40%, preferably less than 30% or less than 20%, or most preferably less than 10%. Recovery in textiles is typically provided by including elastic threads in the textile, for example, elastic polyurethane fibre such as fibres sold under the brand Lycra®. Preferably the textile is free from embedded elastic threads. Low levels or the exclusion of elastic material in the textile helps to prevent or reduce warping, folds or inconsistent behaviour among different mold specimens.

The thickness of the textile is also a consideration in selecting a suitable textile or textiles for the cushion. Thinner textiles provide weight advantages and may stretch more easily over the larger dimension sections of the mold tool. However, internal stresses in thin textiles can cause the textile to shrink or collapse once the cushion is removed from the mold.

The tubular nature of the pre-form 302, 602 reduces the propensity for the pre-form to wrinkle as it is shaped and cured as compared to a flat pre-form 202 because it is more easily able to be deformed to correspond to the shape of the mold tool. However, depending on the properties of the resilient material and the textile material(s), and the desired cushion shape, it may be advantageous for the pre-form to be shaped along the length of the tube to better correspond to the mold shape.

That is, rather than a constant diameter tube, the pre-form may be shaped to reduce the amount of stretching the textile will experience at the widest points of the mold part 35. The predetermined shape of such a pre-form advantageously reduces the prevalence of wrinkles or the occurrence of manufacturing deformities in the composite cushions 5, 105 by reducing the stresses on the textile when it is stretching over the cushion mold tool 35. One exemplary shaped tube pre-form 402 is illustrated in FIG. 14. The radius r of the tube 402 varies along the length of the tube, with wider regions 404, 406 to accommodate the wider parts of the mold positioned so that they will align with the widest parts of the mold inner 35 when the preform is placed over it. For embodiments having inner and outer textile layers, the pre-form tube 402 is foldable about a fold line FL so that when the tube is folded over itself the widest points 404, 406 from opposite sides of the fold line FL are aligned, as shown in FIG. 14(b). The pre-form tube 402 may be symmetrical about the fold line FL.

Figure 15C:
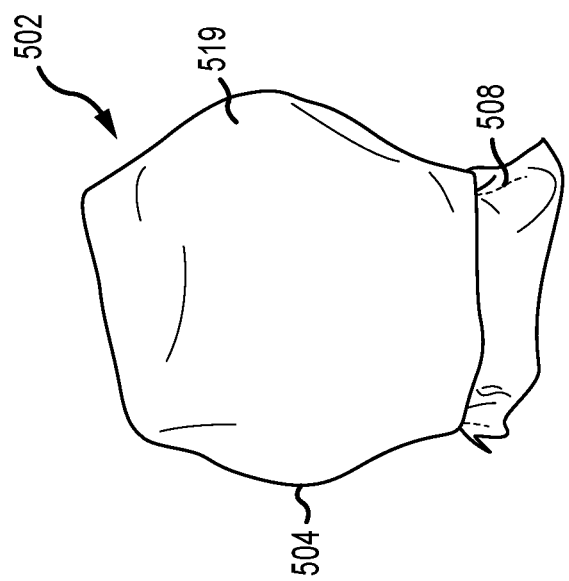
FIGS. 15(a) to 15(c) illustrate an alternative method of forming a contoured pre-form by stitching two sheets together, where
Figure 15B:
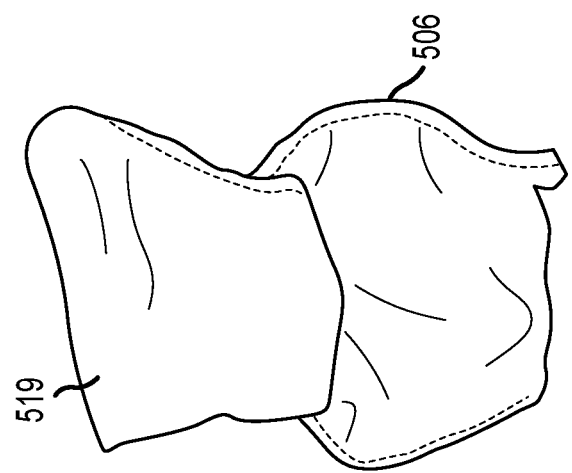
Figure 15A:
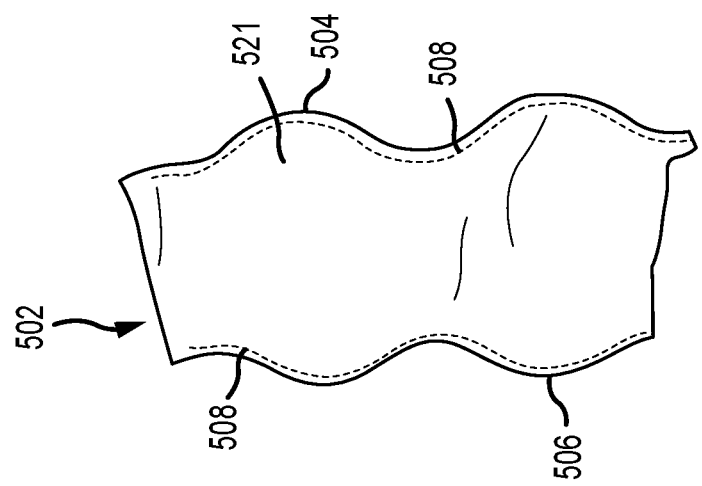

The textile tube 419 is preferably formed as a three-dimensional seam-free tube using a process such as three-dimensional knitting which allows the formation of complex shapes. However, alternatively the textile tube 419 may be created from one or more textile sheets with their edges joined for example, adhered or stitched together as illustrated in FIGS. 15(a) to 15(c). In that embodiment, two textile sheets are cut to shape and laid over each other. The edges are stitched, with the stitching 508 following the desired contour of the tube 502. The textile sheets may be coated with a curable substance or have a curable layer adhered to the sheets before they are stitched together, or the formed tube 502 may be subsequently coated with a curable substance after it is formed.

To form a pre-form having an inner and an outer textile layer, the process described above is once again followed, folding the top of the tube 502 over itself as illustrated in FIGS. 15(b) and 15(c).

Figure 16A:
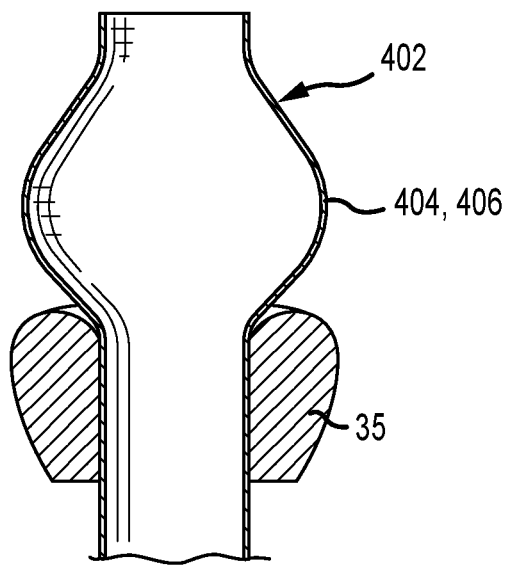
FIGS. 16(a) to 16(d) illustrate a method of placing a contoured pre-form over the inner mold part of FIG. 10(c), where
Figure 16B:
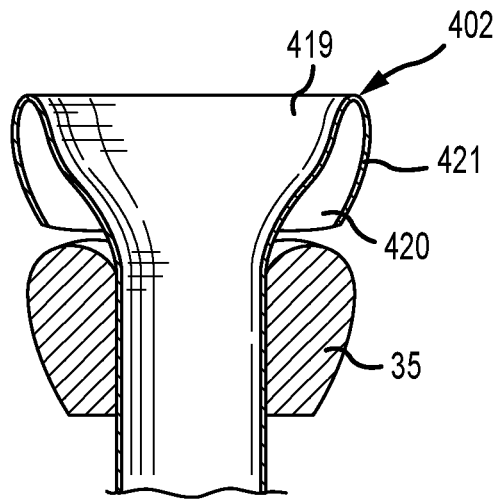
Figure 16C:
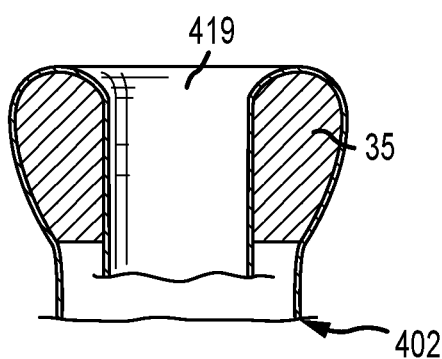
Figure 16D:
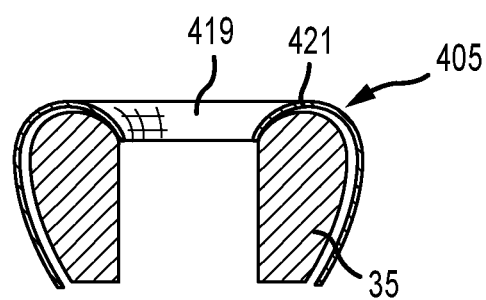
Figure 17C:
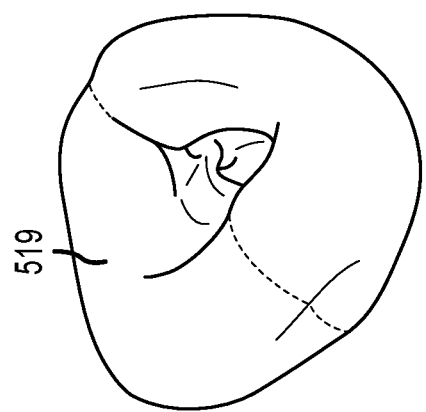
FIGS. 17(a) to 17(c) illustrate a method of placing a contoured stitched pre-form over the inner mold part of FIG. 10(c), where
Figure 17B:
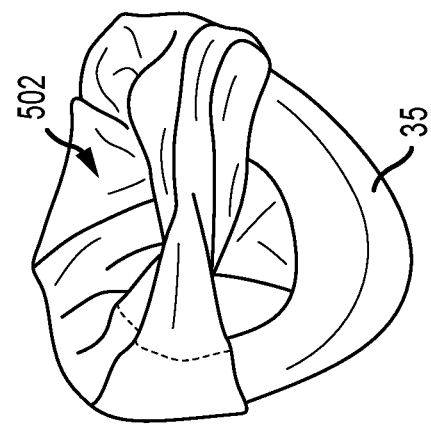
Figure 17A:
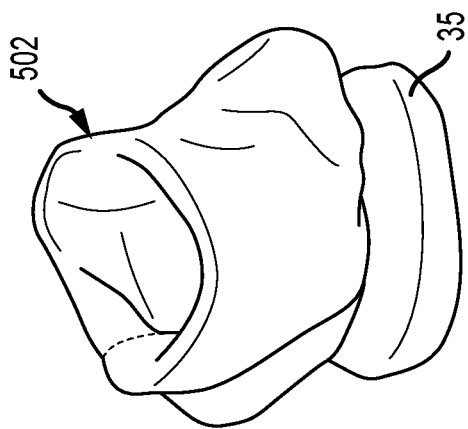
Figure 18C:
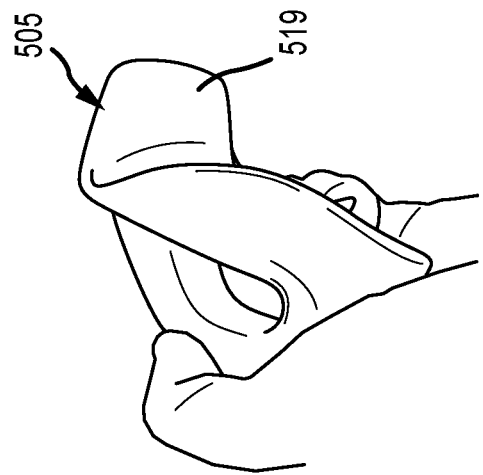
FIGS. 18(a) to 18(c) illustrate a method of creating a cushion from the pre-form and mold arrangement of FIG. 17(c), where
Figure 18B:
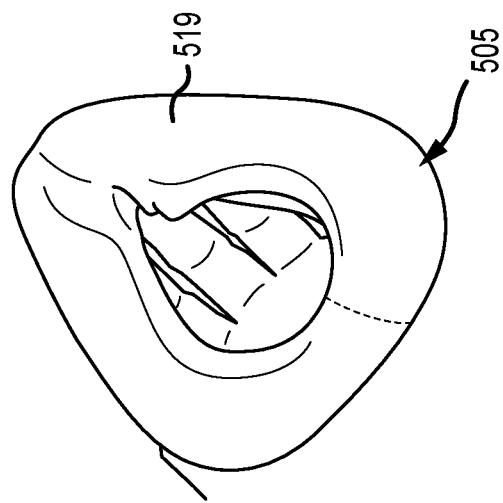
Figure 18A:
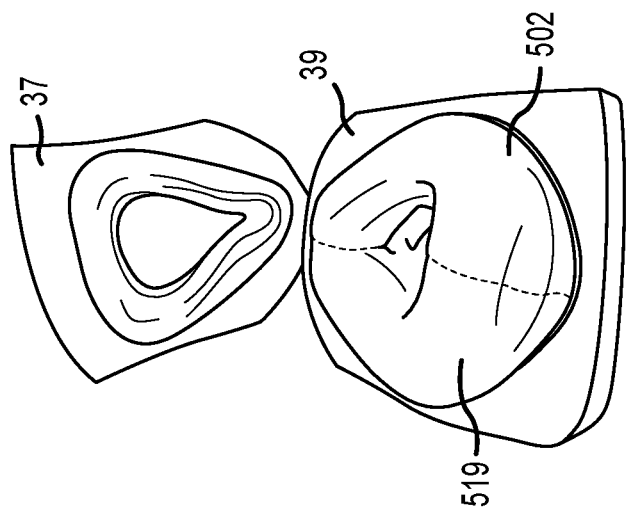

To mold the cushion from the shaped pre-form 402 shown in FIG. 14(b), the pre-form 402 is placed through the opening 41 in the mold inner 35 as shown in FIG. 16(a) and folded over the inner as shown in FIGS. 16(b) and 16(c) with the widest point of the pre-form aligning with the widest point of the mold inner 35. The mold inner 35 is then placed between the outer mold pieces 37, 39 and the mold environment heated to cure the resilient layer 421. Excess material is then removed, for example by cutting it away to form the cushion 405 (FIG. 16(d)).

As a further alternative, rather than a cylindrical pre-form with a constant or varying radius, the tube of the pre-form may have a cross sectional shape that varies along its length to accommodate the shape of the mold. For example, the tube may have a cross sectional shape that transitions from circular to triangular along the length of the textile tube. The cross sectional area of the tube may vary along the length of the textile tube.

Preferred embodiments of the invention have been described by way of example only and modifications may be made thereto without departing from the scope of the invention. For example, in an alternative method, a composite cushion 5, 105 such as those described above may be created using a lay-up method in which multiple layers of pre-formed textile can be layered up to provide different thickness and rigidities in specific areas of the cushion.

As a further alternative a composite cushion 5, 105 such as those described above, may be manufactured using an overmolding technique. For example, the resilient layer 105 is overmolded onto the textile layer 19, 119. This method may be advantageous when relatively thick resilient layers of more than about 1 mm (for example) are desired. The textile layer is placed in a mold tool and silicone injected into the tool.

The invention claimed is:

1. A method of manufacturing a cushion for a respiratory therapy mask for contacting a face of a user, comprising the steps of:
    applying a curable substance to a textile tube to form a cushion pre-form, wherein the textile tube comprises a cylindrical shape formed from at least one sheet of a textile material;
    shaping the cushion pre-form into a cushion profile, and curing the curable substance to bias the cushion towards the cushion profile.

2. The method of claim 1, wherein the curable substance is applied to an outer surface of the textile tube.

3. The method of claim 1, further including the step of placing the pre-form in a mold tool.

4. A method of manufacturing a cushion for a respiratory therapy mask for contacting a face of a user, comprising the steps of:
   applying a curable substance to a textile tube to form a cushion pre-form;
   shaping the cushion pre-form into a cushion profile, wherein the step of shaping the pre-form includes stretching the pre-form over a mold; and
       curing the curable substance to bias the cushion towards the cushion profile.

5. The method of claim 3, further including the step of heating an environment of the mold to cure the curable substance.

6. The method of claim 5, further including the step of removing the cushion pre-form from the mold tool after curing the curable substance, wherein the curing of the curable substance holds the shape of the mold when removed.

7. The method of claim 1, wherein the textile tube comprises a tube with a cross sectional shape that varies along a length of the tube.

8. The method of claim 7, wherein the cross sectional shape transitions from circular to triangular along the length of the textile tube.

9. The method of claim 1, further including the step of removing excess material from the pre-form or cured cushion to facilitate connection of the cushion to a housing of a cushion module.

10. The method of claim 1, wherein the curable substance comprises silicone.

11. The method of claim 1, wherein a radius of the textile tube varies along a length of the tube.

12. A method of manufacturing a cushion for a respiratory therapy mask for contacting a face of a user, comprising the steps of:
   applying a curable substance to a textile tube to form a cushion pre-form;
   shaping the cushion pre-form into a cushion profile, wherein shaping the pre-form includes folding a first end of the textile tube outwards and over the remainder of the length of the textile tube towards a second end of the textile tube, creating a folded double walled textile tube, with the curable substance disposed between the two textile wall layers; and
   curing the curable substance to bias the cushion towards the cushion profile.

13. A method of manufacturing a cushion for a respiratory therapy mask for contacting a face of a user, comprising the steps of:
   applying a curable substance to a textile tube to form a cushion pre-form, wherein the textile tube comprises a knitted textile tube;
   shaping the cushion pre-form into a cushion profile; and
   curing the curable substance to bias the cushion towards the cushion profile.

14. The method of claim 13, wherein the textile tube is formed as a three-dimensional seam-free tube using three-dimensional knitting.

15. The method of claim 4, wherein the pre-form has a shape that corresponds to the shape of a mold over which the pre-form is placed.

16. The method of claim 4, wherein the cross sectional area of the tube varies along a length of the textile tube.

17. The method of claim 16, wherein the cross sectional area varies from a first cross sectional area to a second cross sectional area along the length of the textile tube, the first cross sectional area being larger than the second cross sectional area.

18. The method of claim 4, wherein the textile tube comprises a tube that transitions from a circle of a first radius to a circle of a second radius along a length of the textile tube.

19. The method of claim 18, wherein the first radius is larger than the second radius.

\* \* \* \* \*